US012575744B2

(12) United States Patent
Li et al.

(10) Patent No.: US 12,575,744 B2
(45) Date of Patent: Mar. 17, 2026

(54) DATA PROCESSING DEVICE AND METHOD

(71) Applicant: HON HAI PRECISION INDUSTRY CO., LTD., New Taipei City (TW)

(72) Inventors: Yung-Hui Li, New Taipei City (TW); Latifa Nabila Harfiya, New Taipei City (TW)

(73) Assignee: HON HAI PRECISION INDUSTRY CO., LTD., New Taipei City (TW)

( * ) Notice: Subject to any disclaimer, the term of this patent is extended or adjusted under 35 U.S.C. 154(b) by 337 days.

(21) Appl. No.: 18/316,248

(22) Filed: May 12, 2023

(65) Prior Publication Data

US 2023/0363651 A1 Nov. 16, 2023

Related U.S. Application Data

(60) Provisional application No. 63/364,628, filed on May 13, 2022.

(51) Int. Cl.
*A61B 5/00* (2006.01)
*A61B 5/021* (2006.01)
*A61B 5/024* (2006.01)

(52) U.S. Cl.
CPC .......... *A61B 5/021* (2013.01); *A61B 5/02416* (2013.01); *A61B 5/7257* (2013.01); *A61B 5/7264* (2013.01)

(58) Field of Classification Search
None
See application file for complete search history.

(56) References Cited

U.S. PATENT DOCUMENTS

| | | | | |
|---|---|---|---|---|
| 2013/0085354 A1* | 4/2013 | Hete | .................... | A61B 5/0205 |
| | | | | 600/323 |
| 2014/0257058 A1* | 9/2014 | Clarysse | .............. | A61B 5/7275 |
| | | | | 600/301 |
| 2019/0307337 A1* | 10/2019 | Little | ................. | A61B 5/02141 |
| 2020/0330042 A1* | 10/2020 | Shiue | ................... | A61B 5/0077 |
| 2021/0290091 A1* | 9/2021 | Ramakrishnan | ... | A61B 5/14551 |

* cited by examiner

*Primary Examiner* — Amal Aly Farag
(74) *Attorney, Agent, or Firm* — CKC & Partners Co., LLC

(57) ABSTRACT

A data processing device includes a detection unit, a memory and a processor. The processor performs a short-term Fourier transform on photoplethysmographic data to generate a first spectrogram matrix. The processor also performs numerical split processing on the first spectrogram matrix to generate a first spectrum matrix, where the first spectrum matrix includes first spectrum arrays arranged in sequence from left to right. The processor also inputs the first spectrum arrays into a transformer model from left to right to generate second spectrum arrays in sequence, and transforms the second spectrum arrays into a second spectrum matrix according to an order in which the second spectrum arrays are generated. The processor also performs numerical combining processing on the second spectrum matrix to generate a second spectrogram matrix, and performs an inverse short-term Fourier transform on the second spectrogram matrix to generate arterial blood pressure data.

18 Claims, 9 Drawing Sheets run the transformer model and perform short-term Fourier transform on photoplethysmographic data to generate a first spectrogram matrix ~~ S510 perform numerical split processing on the first spectrogram matrix to generate a first spectrum matrix, where the first spectrum matrix includes multiple first spectrum arrays arranged in sequence from left to right ~~ S520 input multiple first spectrum arrays from left to right into the transformer model to generate multiple second spectrum arrays in sequence, and transform the multiple second spectrum arrays into a second spectrum matrix according to an order in which the multiple second spectrum arrays are generated ~~ S530 perform numerical combining processing on the second spectrum matrix to generate a second spectrogram matrix ~~ S540 perform inverse short-term Fourier transform on the second spectrogram matrix to generate arterial blood pressure data ~~ S550

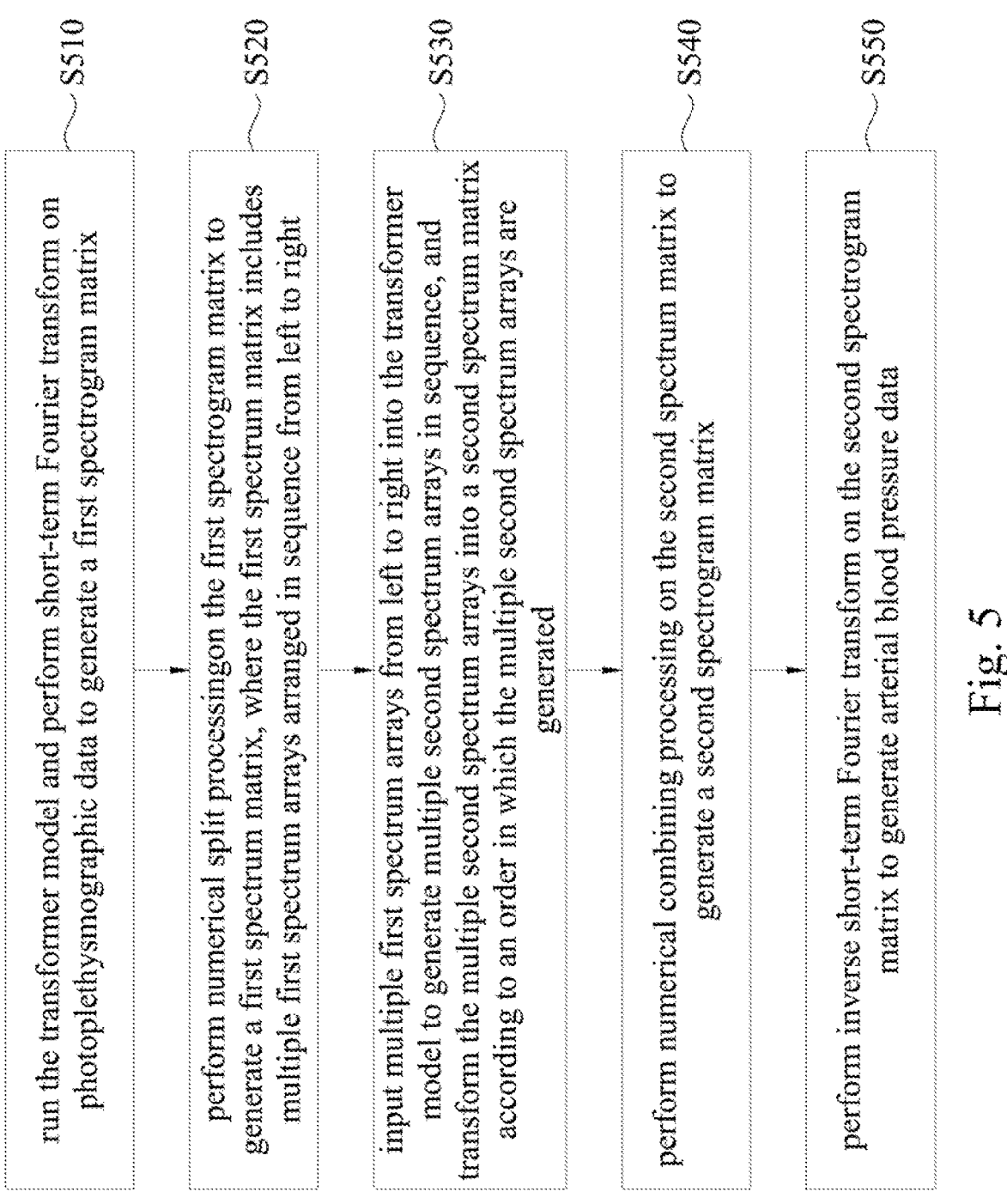

run the transformer model and perform short-term Fourier transform on photoplethysmographic data to generate a first spectrogram matrix ~S510 perform numerical split processing on the first spectrogram matrix to generate a first spectrum matrix, where the first spectrum matrix includes multiple first spectrum arrays arranged in sequence from left to right ~S520 input multiple first spectrum arrays from left to right into the transformer model to generate multiple second spectrum arrays in sequence, and transform the multiple second spectrum arrays into a second spectrum matrix according to an order in which the multiple second spectrum arrays are generated ~S530 perform numerical combining processing on the second spectrum matrix to generate a second spectrogram matrix ~S540 perform inverse short-term Fourier transform on the second spectrogram matrix to generate arterial blood pressure data ~S550

Fig. 5

DATA PROCESSING DEVICE AND METHOD

CROSS-REFERENCE TO RELATED APPLICATION

This application claims priority to U.S. Provisional Application Ser. No. 63/364,628, filed May 13, 2022, which is herein incorporated by reference in its entirety.

BACKGROUND

Field of Invention

The present invention relates to machine learning technology. More particularly, the present invention relates to a data processing device and method.

Description of Related Art

In current medical technology, it is often easier to collect a heart rate of a user than to collect blood pressure of the user. Collecting the heart rate of the user only requires a simple wearable smart bracelet or smart watch, while collecting the blood pressure of the user often requires more sophisticated instruments or invasive devices. Therefore, how to obtain the blood pressure of the user with a simple and low-cost device is an urgent problem for those skilled in the art to solve.

SUMMARY

The invention provides a data processing device, which comprises a detection unit, a memory and a processor. The detection unit is configured for detecting a photoplethysmographic data. The memory is configured for storing a plurality of computer-executable instructions. The processor is coupled to the detection unit and the memory, wherein the processor is configured for executing the plurality of computer-executable instructions to run a transformer model, and configured for performing following operations: performing a short-term Fourier transform on the photoplethysmographic data to generate a first spectrogram matrix, wherein a plurality of columns in the first spectrogram matrix respectively correspond to a plurality of time segments, and each of the plurality of columns in the first spectrogram matrix comprises a plurality of frequency components on a corresponding time segment; performing numerical split processing on the first spectrogram matrix to generate a first spectrum matrix, wherein the first spectrum matrix comprises a plurality of first spectrum arrays arranged in sequence from left to right; inputting the plurality of first spectrum arrays into the transformer model from left to right to generate a plurality of second spectrum arrays in sequence, and transforming the plurality of second spectrum arrays into a second spectrum matrix according to an order in which the plurality of second spectrum arrays are generated; performing numerical combining processing on the second spectrum matrix to generate a second spectrogram matrix; and performing inverse short-term Fourier transform on the second spectrogram matrix to generate arterial blood pressure data.

The invention also provides a data processing method, which comprises: running a transformer model, and performing a short-term Fourier transform on photoplethysmographic data to generate a first spectrogram matrix, wherein a plurality of columns in the first spectrogram matrix respectively correspond to a plurality of time segments, and each of the plurality of columns in the first spectrogram matrix comprises a plurality of frequency components on a corresponding time segment; performing numerical split processing on the first spectrogram matrix to generate a first spectrum matrix, wherein the first spectrum matrix comprises a plurality of first spectrum arrays arranged in sequence from left to right; inputting the plurality of first spectrum arrays into the transformer model from left to right to generate a plurality of second spectrum arrays in sequence, and transforming the plurality of second spectrum arrays into a second spectrum matrix according to an order in which the plurality of second spectrum arrays are generated; performing numerical combining processing on the second spectrum matrix to generate a second spectrogram matrix; and performing inverse short-term Fourier transform on the second spectrogram matrix to generate arterial blood pressure data.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows:

FIG. 5 is a flow chart of a data processing method disclosed in the present disclosure.

DETAILED DESCRIPTION

Figure 1:
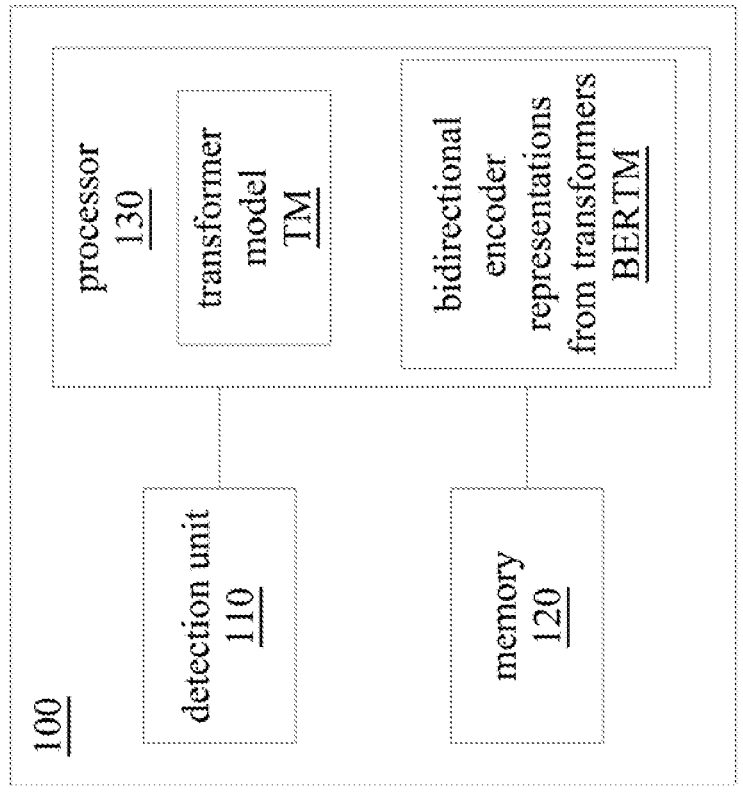
FIG. 1 is a block diagram of a data processing device disclosed in the present disclosure.

Reference will now be made in detail to the present embodiments of the invention, examples of which are illustrated in the accompanying drawings. Wherever possible, the same reference numbers are used in the drawings and the description to refer to the same or like parts.

Reference is made to FIG. 1, which is a block diagram of a data processing device 100 disclosed in the present disclosure. The data processing device 100 includes a detection unit 110, a memory 120 and a processor 130. The data processing device 100 can calculate, train and use a transformer model TM.

In some embodiments, the data processing device 100 can be implemented by various pulse oximetry devices. For example, wearable smart bracelets or smart watches, etc.

In some embodiments, the memory 120 is used for storing computer-executable instructions, training data (during the training phase of the transformer model TM), learnable parameters of the transformer model TM, input data that needs to be processed by the transformer model TM and/or output data produced by the transformer model TM. In some embodiments, the memory 120 can be implemented by random access memory module, read only memory module, flash memory, hard disk, cache memory, static random access memory, dynamic random access memory, non-volatile memory, solid state hard disk, optical storage media, or other equivalent storage components. In some embodiments, the memory 120 stores instructions executable by the processor 130 for performing detailed steps described in subsequent paragraphs.

The processor 130 is coupled to the memory 120. The processor 130 is used for executing computer-executable instructions to calculate, train or operate the transformer model TM. In some embodiments, the transformer model TM is used for performing various natural language tasks or image processing, such as question answering, document classification, name extraction, contextual coherence parsing, natural language reasoning, document summarization, translation, image recognition, image classification, image prediction or image transforming, etc. In one example, when the transformer model TM is used for performing a sequence-to-sequence task, the processor 130 will transmit an input vector sequence to the transformer model TM, the transformer model TM transforms the input vector sequence into an output vector sequence, where the input vector sequence and the output vector sequence both include a series of vector expressions. In some embodiments, the transformer model TM can include an encoder module and a decoder module, where the encoder module can include multiple first hidden representation layers, and the decoder module can include multiple second hidden representation layers.

In some embodiments, the processor 130 is further configured for executing the computer-executable instructions to calculate, train or operate a bidirectional encoder representations from transformers (BERT) model BERTM. In some embodiments, the BERT Model BERTM can be used for pre-training the encoder module in the transformer model TM. In this way, when using the transformer model TM to perform downstream tasks, the time and resources consumed by the training of the transformer model TM can be greatly reduced.

In some embodiments, the processor 130 can include a graphics processing unit (GPU), an application specific integrated circuit (ASIC), a field programmable gate array (FPGA), tensor processing unit (TPU), digital signal processor (DSP), single-instruction multiple-data (SIMD) processor and/or any equivalent processing circuit. Typically, such processors can accelerate various computational tasks related to estimation of neural network models (e.g., training, predicting, preprocessing, etc.) compared to general-purpose central processing units (CPUs), where its acceleration effect can reach an order of magnitude or more.

The detection unit 110 is coupled to the processor 130. The detection unit 110 can be any detection circuit for detecting photoplethysmographic data (PPG). For example, the detection unit 110 can be a detection circuit including a microprocessor, a light-emitting diode (LED) and a photo-receptor, where the light-emitting diode is used for illuminating wrist skin of a user, and the photoreceptor (e.g., a charge-coupled device (CCD) or a complementary metal oxide semiconductor (CMOS) active pixel sensor) is used for detecting light intensity reflected by the wrist skin of the user, and a microprocessor is used for calculating the photoplethysmographic data from the light intensity.

In some embodiments, the data processing device 100 is not limited to include the detection unit 110, the memory 120 and the processor 130, and the image processing device 100 can further include other elements required for operation and application. For example, the data processing device 100 can further include an output interface (e.g., a display panel for displaying information), an input interface (e.g., a touch panel, a keyboard, a microphone, a scanner or a flash memory reader), and a communication circuit (e.g., Wi-Fi communication model, Bluetooth communication model, wireless telecommunication network communication model, etc.). For example, the output interface can receive output results generated by the transformer model TM.

Figure 2:
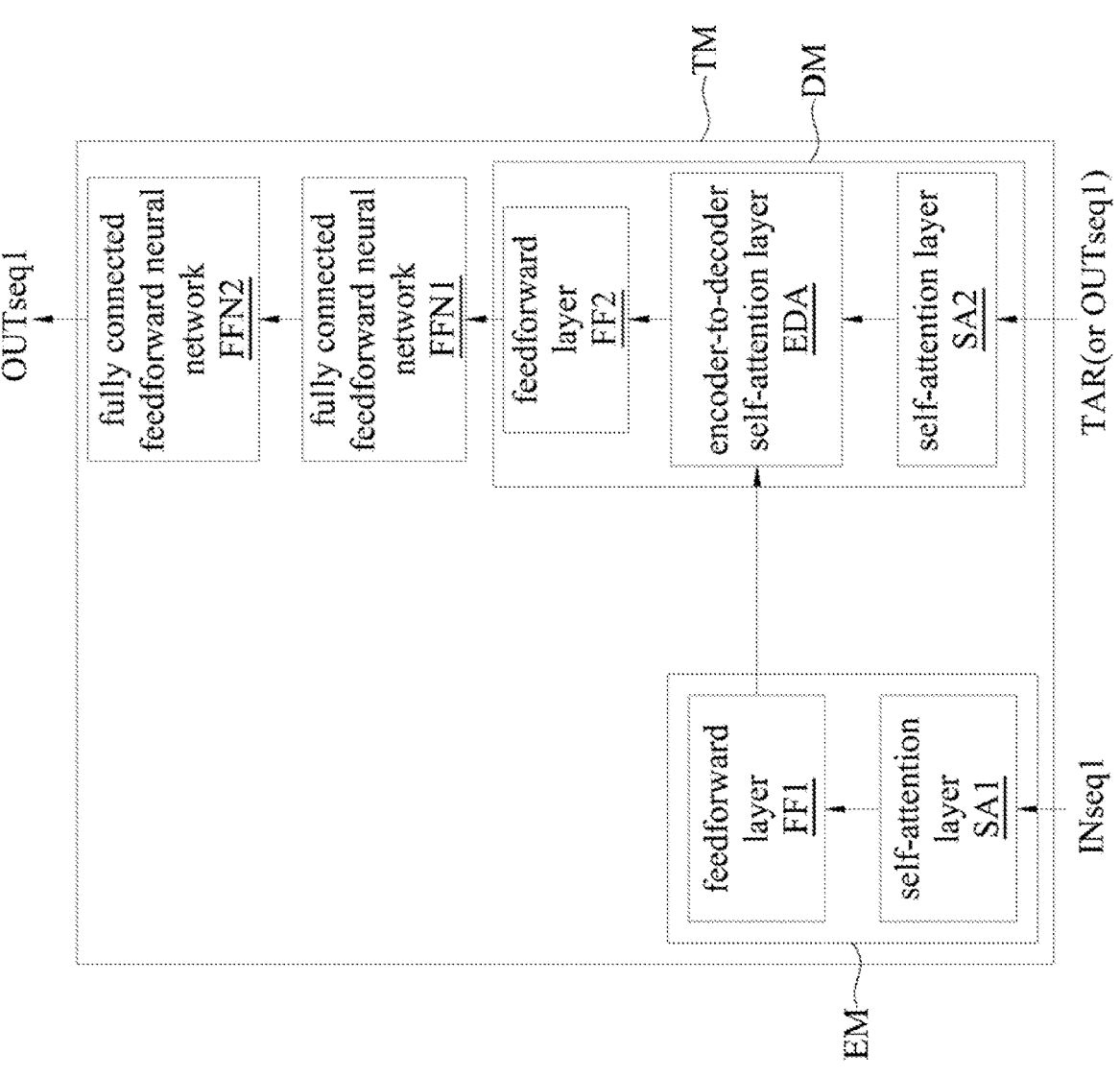
FIG. 2 is a schematic diagram of neural network architecture of a transformer model according to some embodiments of the present disclosure.

Reference is made to FIG. 2 further, which is a schematic diagram of neural network architecture of the transformer model TM according to some embodiments of the present disclosure. As shown in FIG. 2, the transformer model TM includes an encoder module EM and a decoder module DM.

The encoder module EM is used for generating an encoded representation according to an input vector sequence INseq1. The decoder module DM is used for generating or predicting an output vector sequence OUTseq1 according to an encoded expression generated by the encoder module EM.

In an exemplary example, assume that an image is split into 5 equal column arrays, and these column arrays are transformed into the input vector sequences INseq1 from left to right (e.g., performing a method of transforming a first multiple spectral array), and its sequence length is 10. All vector representations in the input vector sequence INseq1 adopt 100-dimensional vector representations (e.g., 1×100 matrix). In this case, the 5 column arrays can be transformed to an input representation of dimension 10×100. Similarly, if an image contains a 2048 column arrays, the input vector sequence INseq1 will be represented as an input representation of dimension 4096×100.

In some embodiments, the transformer model TM includes fully connected feedforward neural networks FFN1-FFN2, which are coupled with the decoder module DM. In some embodiments, according to an output matrix generated by the decoder module DM, the fully connected feedforward neural networks FFN1-FFN2 generate the output sequence OUTseq1 accordingly.

Figure 6:
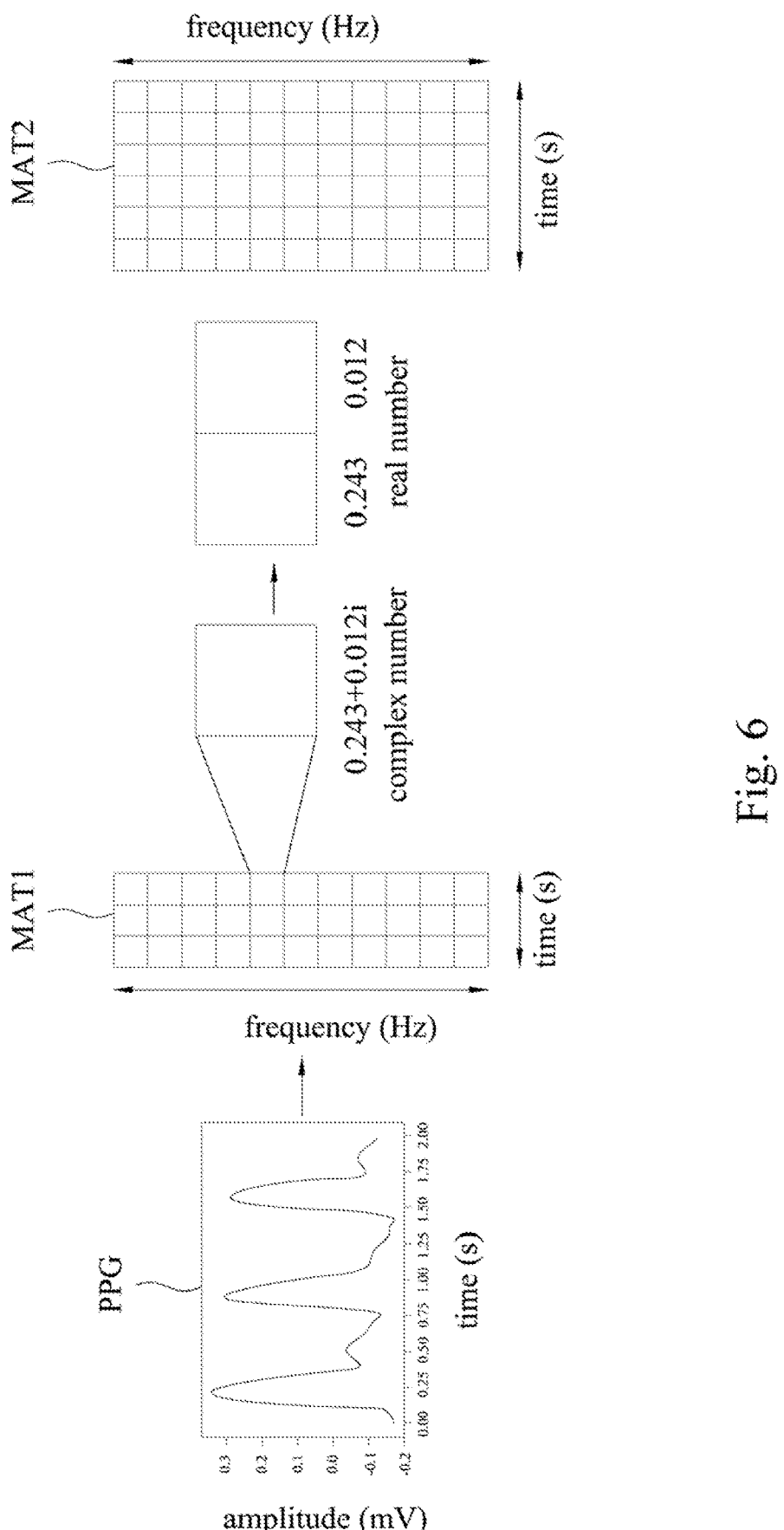
FIG. 6 is a schematic diagram of numerical split processing according to some embodiments of the present disclosure.

In some embodiments, the transformer model TM is used for receiving the output vector sequence OUTseq1 or a target vector sequence TAR (For example, in another image corresponding to the above image, a series of column arrays are cut out, and the method of generating multiple first spectrum arrays in the following FIG. 6 is also performed to transformed a series of column arrays into the target vector sequence TAR).

As shown in FIG. 2, in some embodiments, the encoder module EM includes a self-attention layer SA1 and a feedforward layer FF1 (i.e., the above-mentioned multiple first hidden representation layers), and the decoder module DM includes an self-attention layer SA2 (or called a masked self-attention layer), encoder-to-decoder self-attention layer EDA (or called cross-attention layer) and a feedforward layer FF2 (i.e., the above-mentioned multiple second hidden representation layers). In these layers, the self-attention layer SA1, the self-attention layer SA2 and the encoder-todecoder self-attention layer EDA are used for finding out attention relationship between different tags (e.g., a corresponding column array in the input vector sequence INseq1 or the output vector sequence OUTseq1), and the feedforward layer FF1 and the feedforward layer FF2 have structures and functions similar to the above-mentioned fully connected feedforward neural networks FFN1-FFN2, respectively, where the feedforward layer FF1 and the feedforward layer FF2 are respectively used as structural layers for transforming an output of the self-attention layer SA1 and the encoder-to-decoder self-attention layer EDA. In addition, with the structures of the feedforward layer FF1 and the feedforward layer FF2, it is easier to make the sequences output respectively by the feedforward layer FF1 and the feedforward layer FF2 complete the training of the entire transformer model TM. If the structures of the feedforward layer FF1 and the feedforward layer FF2 are not adopted, the training of the transformer model TM can be more unstable (i.e., the training cannot be completed).

Figure 3:
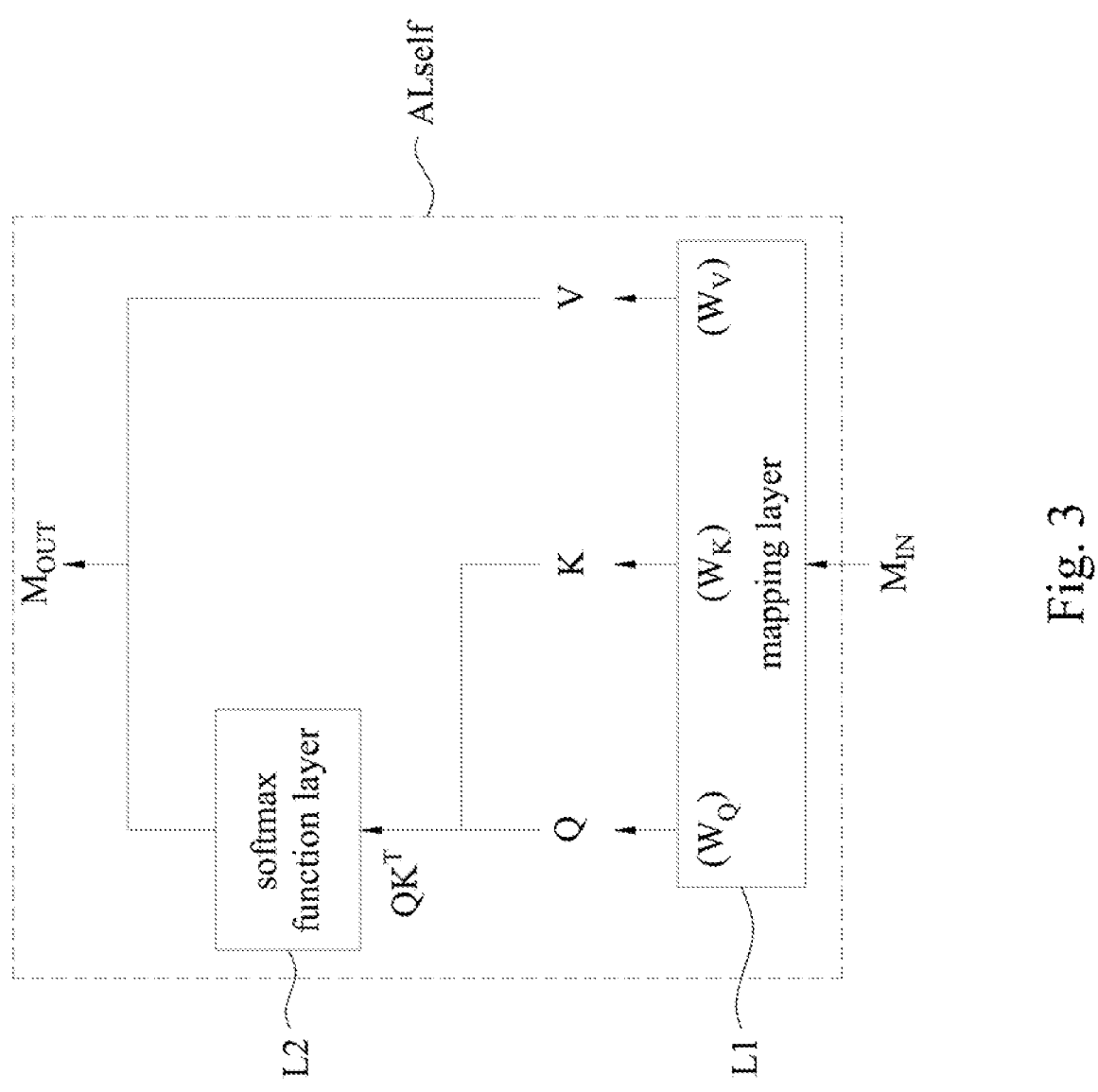
FIG. 3 is a schematic diagram of an internal structure of a self-attention layer using a self-attention mechanism in some embodiments of the present disclosure.

Reference is made to FIG. 3, which is a schematic diagram of an internal structure of a self-attention layer ALself using a self-attention mechanism in some embodiments of the present disclosure. In some practical cases, the self-attention layer ALself using the self-attention mechanism can be used in at least one (or each) of the self-attention layer SA1, the self-attention layer SA2 and the encoder-to-decoder self-attention layer EDA. In some embodiments, the self-attention layer ALself is implemented by program instructions executed by the processor 130 shown in FIG. 1.

It should be noted that although the above-mentioned embodiment adopts the encoder module EM and the decoder module DM, in practical applications, more encoder modules EM and more decoder modules DM can be used.

As shown in FIG. 3, the self-attention layer ALself using the self-attention mechanism includes a mapping layer L1 and a softmax function layer L2.

The self-attention layer ALself using the self-attention mechanism allows a tag to pay attention to all other tags in the entire sequence, and combines information from the other tags. The mapping layer L1 corresponding to an input matrix MIN of the input vector sequence is processed by three linear mappings (applying three learnable weights $W_Q$, $W_K$ and $W_V$) respectively to send out a query vector, a key vector and a value vector.

In some embodiments, a dimension of an input matrix MIN is n×d, where n is a sequence length of the input vector sequence INseq1, and d is a dimension value of a feature vector in the input vector sequence INseq1. For example, when the input vector sequence INseq1 contains 2048 column arrays, and each column array in the input vector sequence INseq1 is mapped to a 100-dimensional vector representation, the input matrix MIN will be a 2048×100 matrix (n=2048, d=100). Due to parallel processing, the query vector generated by the mapping layer L1 will be packed into a query matrix Q of n×d dimensions. Similarly, the key vector and the value vector are packed into a key matrix K with n×d dimensions and a value matrix V with n×d dimensions, respectively.

An output matrix $M_{OUT}$ generated by the self-attention layer ALself using the self-attention mechanism is defined as:

$$M\_OUT = self\_attention(Q, K, V) = softmax\left(\frac{QK^T}{\sqrt{d}}\right)V \quad \text{equation (1)}$$

In equation (1), the self-attention matrix $QK^T$ is a product between the query matrix Q and a transposed key matrix $K^T$ of the key matrix K. The self-attention matrix $QK^T$ holds attention values between all paired tags and associates all tags of the entire sequence with each other. The self-attention matrix $QK^T$ is divided by a scaling factor $\sqrt{d}$ and passed to the softmax function layer L2. An output of the softmax function layer L2 is $$softmax\left(\frac{QK^T}{\sqrt{d}}\right)$$

representing all attention weights between the query vector and all key vectors, and the output of the softmax function layer L2 is linearly combined with the value matrix V to generate the output matrix $M_{OUT}$.

In the calculation procedure of generating the output matrix $M_{OUT}$ above, the softmax function layer L2 is calculated according to the self-attention matrix $QK^T$. In this case, the query matrix Q is a matrix of n×d dimensions, and the transposed key matrix $K^T$ of the key matrix K is a matrix of d×n dimensions, so the self-attention matrix $QK^T$ is a matrix of n×n dimensions.

Figure 4:
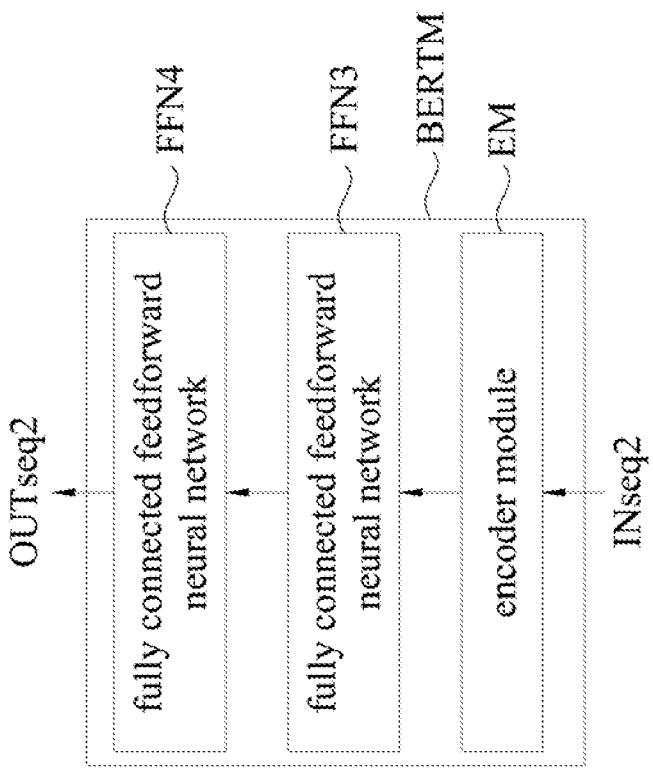
FIG. 4 is a schematic diagram of an internal structure of a bidirectional encoder representations from transformers (BERT) model according to some embodiments of the present disclosure.

Reference is made to FIG. 4, which is a schematic diagram of an internal structure of the BERT model BERTM according to some embodiments of the present disclosure. As shown in FIG. 4, the BERT model BERTM includes the encoder module EM and fully connected feedforward neural networks FFN3-FFN4.

In some embodiments, the encoder EM is included in the above-mentioned transformer model TM, where the BERT model BERTM can be used for pre-training the encoder module EM. In some embodiments, the encoder module EM is used for generating the encoded representation according to the input vector sequence INseq2. It should be noted that the input vector sequence INseq2 can also be generated by using the method of generating the multiple first spectrum arrays in FIG. 6 below.

In some embodiments, the fully connected feedforward neural networks FFN3-FFN4 are connected in sequence, and the fully connected feedforward neural network FFN3 is coupled with the encoder module EM. In some embodiments, according to the output matrix generated by the encoder module EM, the fully connected feedforward neural networks FFN3-FFN4 generate the output vector sequence OUTseq2 accordingly. In some embodiments, the BERT model BERTM can perform a loss function calculation on the arrays corresponding to the above-mentioned inserted column arrays in the output vector sequence OUTseq2 to complete the pre-training of the encoder module EM.

Reference is made to FIG. 5, which is a flowchart of a data processing method disclosed in the present disclosure. The data processing device 100 shown in FIG. 1 can be used for performing all steps in the data processing method in FIG. 5.

As shown in FIG. 5, firstly, in step S510, the transformer model is run, and the photoplethysmographic data is performed by short-term Fourier transform (STFT) to generate the first spectrogram matrix. In detail, the processor performs the STFT on the photoplethysmographic data to generate the first spectrogram matrix, multiple columns in the first spectrogram matrix correspond to multiple time segments respectively, and each of the multiple columns in the first spectrogram matrix includes multiple frequency components on a corresponding time segment. In other words, one column corresponds to one time segment, and one element in one column corresponds to one frequency.

In some embodiments, the processor can perform signal preprocessing on the photoplethysmographic data, so as to perform the STFT on the processed photoplethysmographic data. In some embodiments, the signal preprocessing includes bandpass filter processing, Z-score normalization processing, peak and foot detection of photoplethysmography, signal segmentation processing, abnormal waveform removal processing and resampling processing.

In some embodiments, an encoder module in the transformer model is used for inputting the multiple first spectrum arrays. In some embodiments, each of the multiple columns in the first spectrogram matrix includes multiple complex numbers respectively corresponding to multiple frequencies.

In step S520, numerical split processing is performed on the first spectrogram matrix to generate a first spectrum matrix, where the first spectrum matrix includes multiple first spectrum arrays arranged in sequence from left to right. In some embodiments, the numerical split processing includes: one of the multiple columns in the first spectrogram matrix is selected from left to right, the multiple complex numbers of the one of the multiple columns are split into multiple real part values and multiple imaginary part values, a real number spectrum array and an imaginary number spectrum array are generated according to the multiple real part values and the multiple imaginary part values, a real number spectrum array is used as the one of the columns, and the imaginary number spectrum array is inserted to right of the one of the multiple columns.

In step S530, the multiple first spectrum arrays are input into the transformer model from left to right to generate multiple second spectrum arrays in sequence, and the multiple second spectrum arrays are transformed into a second spectrum matrix according to an order in which the multiple second spectrum arrays are generated. In some embodiments, the fully connected feedforward neural network is used for outputting the multiple second spectrum arrays.

In step S540, numerical combining processing is performed on the second spectrum matrix to generate a second spectrogram matrix. In some embodiments, the numerical combining processing includes: two columns in the second spectrum matrix are selected in sequence from left to right. Next, multiple values of leftmost one of the two selected columns are used as the real part values of multiple complex numbers, and multiple values of rightmost one of the two selected columns are used as the imaginary part values of the multiple complex numbers, where the multiple complex numbers correspond to the multiple frequencies respectively. Next, for the two selected columns, a combined spectrum array is generated according to the multiple frequencies and the multiple complex numbers. Next, for the two selected columns, the combined spectrum array is used as the leftmost one of the two columns in the second spectrum matrix, and the rightmost one of the two columns in the second spectrum matrix is deleted.

In step S550, inverse STFT is performed on the second spectrogram matrix to generate arterial blood pressure (ABP) data. In some embodiments, the ABP data is used for indicating blood pressure of the user.

In some embodiments, the BERT model is further run, and the BERT model is used for performing: one of the multiple first spectrum arrays is replaced with a masked array to generate a masked spectrum matrix. Next, the one of the first spectrum arrays is replaced with a random array to generate a random spectrum matrix. Next, the masked spectrum matrix, the random spectrum matrix and the first spectrum matrix is input into an encoder module in the transformer model to pre-train the encoder module. In some embodiments, each element in the masked array can be the same real number. In some embodiments, each element in the random array can be any real number.

It should be noted that detailed steps will be further described in following examples.

Reference is made to FIG. 6, which is a schematic diagram of the numerical split processing according to some embodiments of the present disclosure. As shown in FIG. 6, the photoplethysmographic data PPG can be performed by STFT to generate the first spectrogram matrix MAT1, and for example, the first spectrogram matrix MAT1 can be split into a matrix of 11×3, where these elements are all corresponding to their respective frequencies, and each element is sampled to obtain a complex value, for example, 0.243+0.012i. Next, the real part value (0.243) and the imaginary part value (0.012) of this element are taken out, and the value of this element is set as the real part value, and a new element on the right side of this element is inserted, where the value of this new element is set as the imaginary part value. In this way, the second spectrum matrix MAT2 can be generated, and its dimension is 11×6.

It should be noted that the numerical combining processing described in the preceding paragraphs is reverse processing of the above-mentioned numerical split processing. In other words, for the second spectrum matrix, two adjacent columns are combined from left to right, and the left column of the two columns is used as the real part value and the right column is used as the imaginary part value to generate a complex number as the value of the left column, thereby deleting the right column. In this way, a second spectrogram matrix is further generated, and an inverse STFT is performed on the second spectrogram matrix to generate ABP data.

Figure 7:
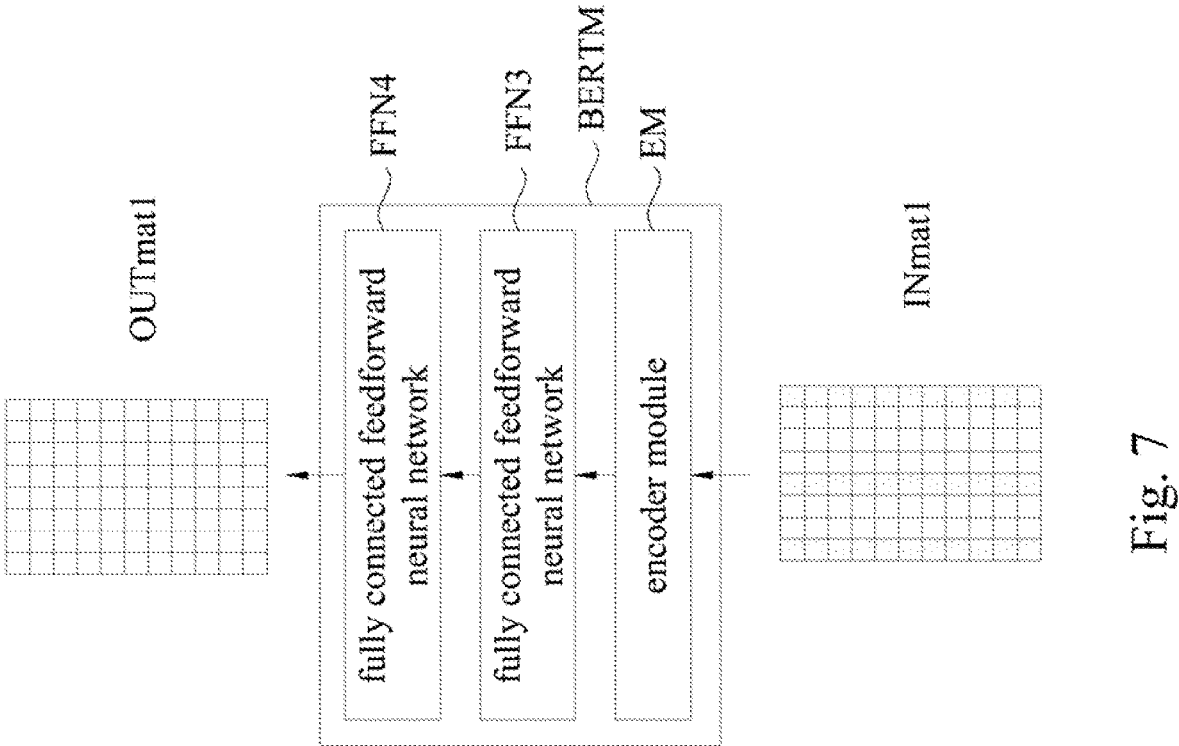
FIG. 7 is a schematic diagram of performing the BERT model according to some embodiments of the present disclosure.

Reference is made to FIG. 7, which is a schematic diagram of performing the BERT model BERTM according to some embodiments of the present disclosure. As shown in FIG. 7, a fourth column in the input matrix INmat1 can be replaced as a masked array (e.g., a value of each element is −0.99999), or the fourth column in the input matrix INmat1 can be replaced as a random array (e.g., a value of each element is any value in a specific value range), and it is also possible not to perform any processing on the input matrix INmat1. It should be noted that in practice, there will be multiple input matrices INmat1 to pre-train the encoder module EM, where 15% of these input matrices INmat1 will be specially processed (e.g., 15 input matrices INmat1 will be specially processed among 100 input matrices INmat1), where in the specially processed input matrices INmat1, 80% will be inserted into the above-mentioned masked array, 10% will be inserted into the above-mentioned random array, and 10% will not be processed. In addition, a first column and a last column in the input matrix INmat1 are usually set as a start column (e.g., all elements are −1) and an end column (e.g., all elements are 1) respectively. A second column to a penultimate column in the input matrix INmat1 can be the above-mentioned first spectrum matrix.

Furthermore, each column in the input matrix IMmat1 can be input to the BERT model BERTM in sequence, where the BERT model BERTM includes an encoder module EM and fully connected feedforward neural networks FFN3-FFN4. The fully connected feed-forward neural network FFN4 can output multiple arrays. Next, the generated first and last arrays (i.e., a start array and an end array) are removed, and remaining arrays are sequentially combined into an output matrix OUTmat1. Next, cross entropy calculation can be performed on the output matrix OUTmat1 and the input matrix INmat1 to generate a loss, and this loss is used for performing back propagation processing on the BERT model BERTM to update parameters in the encoder module EM, thereby completing the pre-training of the encoder module EM.

Figure 8:
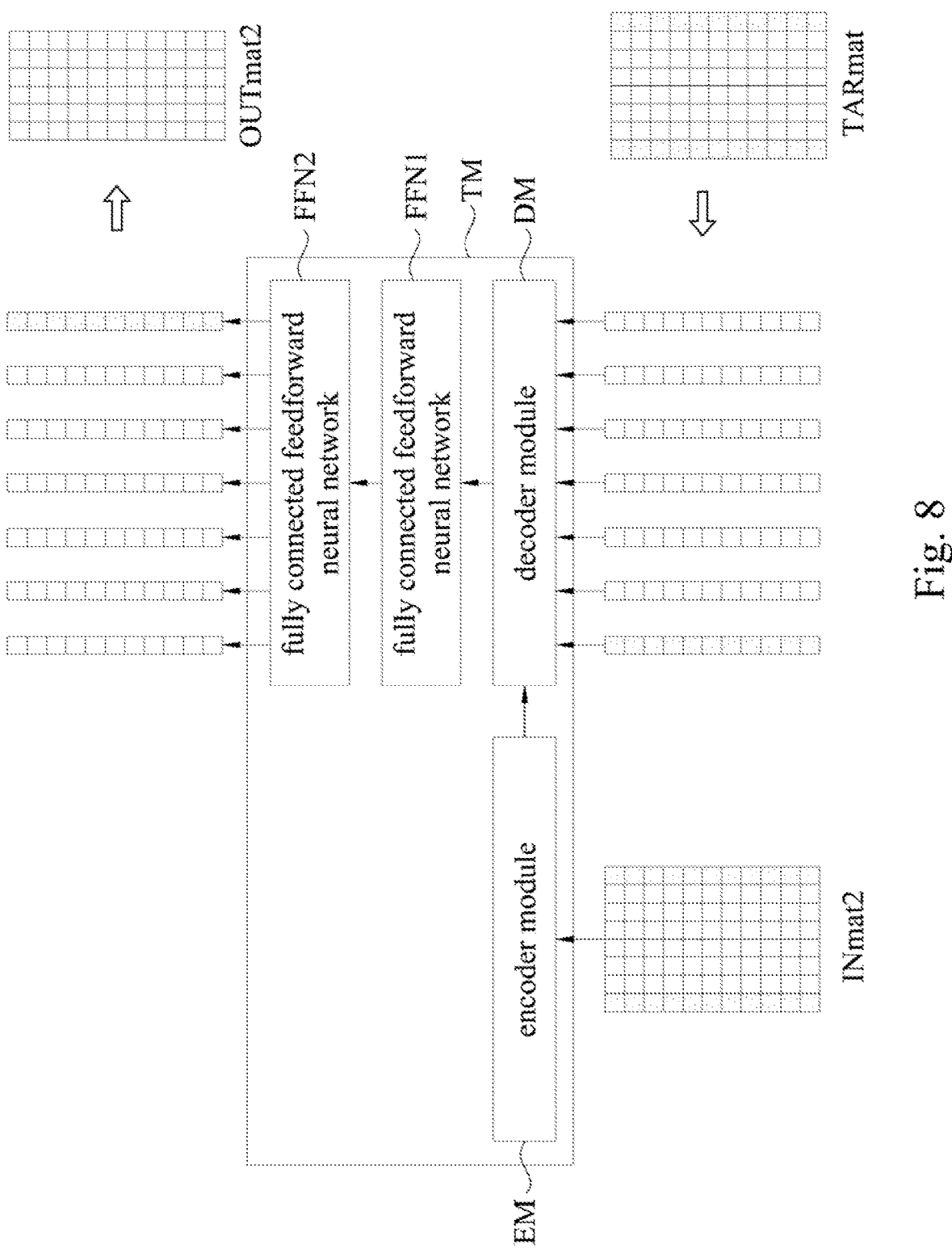
FIG. 8 is a schematic diagram of training the transformer model according to some embodiments of the present disclosure.

Reference is made to FIG. 8, which is a schematic diagram of training the transformer model TM according to some embodiments of the present disclosure. As shown in FIG. 8, each column in an input matrix INmat2 is sequentially input to an input encoder module EM. Next, each column in a target matrix TARmat can be sequentially input to a decoder module DM, and through processing of the decoder module DM and the fully connected feedforward neural networks FFN1-FFN2, multiple arrays are generated sequentially from the fully connected feedforward neural network FFN2. Next, a last array is removed, and the remaining arrays are sequentially combined into an output matrix OUTmat2.

It should be noted that the first column and the last column in the input matrix INmat2 are also respectively set as the start column (e.g., all elements are −1) and the last column (e.g., all elements are 1). A second column to a penultimate column in the input matrix INmat2 can be the above-mentioned first spectrum matrix.

A first column and a last column in the target matrix TARmat are also respectively set as the start column (e.g., all elements are −1) and the last column (e.g., all elements are 1). A second column to a penultimate column in the target matrix TARmat can be a blood pressure spectrum matrix. The blood pressure spectrum matrix is generated by signal preprocessing and STFT on target ABP data, where the target ABP data is used as the ground truth of the photoplethysmographic data. In other words, the target ABP data and the photoplethysmographic data are respectively detected from the same user in advance (e.g., the same user is detected by using a sphygmomanometer and a smart wristband).

Furthermore, root-mean-square error (RMSE) processing can be performed on the output matrix OUTmat2 and the blood pressure spectrum matrix to generate a loss, and this loss is used for performing the backpropagation processing on the transformer model TM to update the parameters in the encoder module EM and decoder module DM, thereby completing the training of the transformer model TM.

Figure 9:
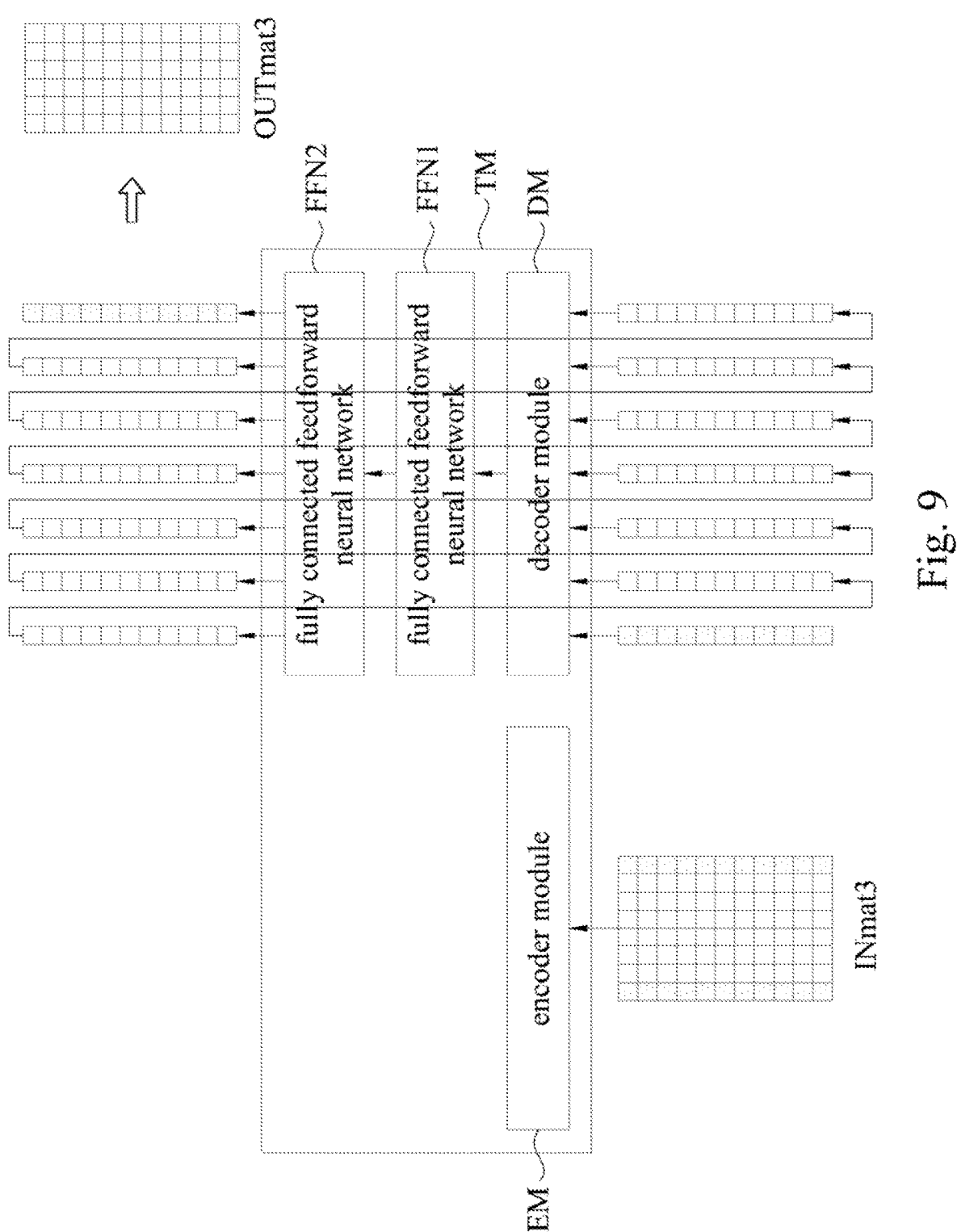
FIG. 9 is a schematic diagram of using the transformer model in some embodiments of the present disclosure.

Reference is made to FIG. 9, which is a schematic diagram of using the transformer model TM in some embodiments according to the present disclosure. As shown in FIG. 9, each column in an input matrix INmat3 is input to the encoder module EM in sequence. Next, a start array (e.g., all elements are −1) can be input to the decoder module DM, and processed by the decoder module DM and the fully connected feedforward neural networks FFN1-FFN2 to generate a first array from the fully connected feedforward neural network FFN2. Next, the generated first array will be input to the decoder module DM, and processed by the decoder module DM and the fully connected feedforward neural networks FFN1-FFN2, so as to generate a second array from the fully connected feedforward neural network FFN2. By analogy, continue to input the generated second array to the decoder module DM until the fully connected feedforward neural network FFN2 generates an end array (e.g., all elements are 1). Next, the end array is removed, and these arrays are combined in sequence to generate an entire output matrix OUTmat3 according to time segments for generating each array.

At this time, a first column and a last column in the input matrix INmat3 are also respectively set as the start column (e.g., all elements are −1) and the end column (e.g., all elements are 1). A second column to a penultimate column in the input matrix INmat3 can be the above-mentioned first spectrum matrix.

Finally, all the columns in the output matrix OUTmat3 can be performed by the above-mentioned numerical combining processing and the above-mentioned inverse STFT to generate the arterial blood pressure data required by the user.

In summary, the data processing device disclosed in the present disclosure only needs to collect the photoplethysmographic data of the user and can use the transformer model to generate the ABP data required by the user. Therefore, only a detection unit with a very simple and low-cost circuit is required to detect the photoplethysmographic data to predict the ABP data, which will reduce the high cost of directly collecting the ABP data of the user. In addition, the encoder module in the transformer model can be pre-trained using the BERT model based on the photoplethysmographic data of the user, and this will greatly reduce the training time of the transformer model and greatly increase the accuracy of the transformer data.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A data processing device, comprising:
a detection circuit configured for detecting photoplethysmographic data, the detection circuit comprising:
a light-emitting diode used for illuminating wrist skin of a user;
a photoreceptor used for detecting light intensity reflected by the wrist skin of the user; and
a microprocessor used for calculating the photoplethysmographic data from the light intensity;
a memory configured for storing a plurality of computer-executable instructions; and
a processor coupled to the detection circuit and the memory, wherein the processor is configured for executing the plurality of computer-executable instructions to run a transformer model, and configured for performing following operations:
performing a short-term Fourier transform on the photoplethysmographic data to generate a first spectrogram matrix, wherein a plurality of columns in the first spectrogram matrix respectively correspond to a plurality of time segments, and each of the plurality of columns in the first spectrogram matrix comprises a plurality of frequency components on a corresponding time segment;
performing numerical split processing on the first spectrogram matrix to generate a first spectrum matrix, wherein the first spectrum matrix comprises a plurality of first spectrum arrays arranged in sequence from left to right;
inputting the plurality of first spectrum arrays into the transformer model from left to right to generate a plurality of second spectrum arrays in sequence, and transforming the plurality of second spectrum arrays into a second spectrum matrix according to an order in which the plurality of second spectrum arrays are generated, wherein the second spectrum arrays are columns in the second spectrum matrix from left to right;

performing numerical combining processing on the second spectrum matrix to generate a second spectrogram matrix; and performing inverse short-term Fourier transform on the second spectrogram matrix to generate arterial blood pressure data.

2. The data processing device of claim 1, wherein the transformer model comprises an encoder module, a decoder module, a first fully connected feedforward neural network and a second fully connected feedforward neural network, wherein the encoder module is configured for inputting the plurality of first spectrum arrays, and connected to the decoder module, and the decoder module is connected to the first fully connected feedforward neural network, and the first fully connected feedforward neural network is connected to the second fully connected feedforward neural network, and the second fully connected feedforward neural network is configured for outputting the plurality of second spectrum arrays, wherein the encoder module comprises a plurality of first hidden representation layers, and the decoder module comprises a plurality of second hidden representation layers.

3. The data processing device of claim 2, wherein the plurality of first hidden representation layers comprise a first self-attention layer and a first feedforward layer, and the plurality of second hidden representation layers comprise a second self-attention layer, an encoder-to-decoder self-attention layer and a second feedforward layer.

4. The data processing device of claim 1, wherein each of the plurality of columns in the first spectrogram matrix comprises a plurality of complex numbers respectively corresponding to the plurality of frequency components, wherein the numerical split processing comprises:

selecting one of the plurality of columns in the first spectrogram matrix from left to right, splitting the plurality of complex numbers of the one of the plurality of columns into a plurality of real part values and a plurality of imaginary part values, generating a real number spectrum array and an imaginary number spectrum array according to the plurality of real part values and the plurality of imaginary part values, using the real number spectrum array as the one of the columns, and inserting the imaginary number spectrum array to right of the one of the plurality of columns.

5. The data processing device of claim 1, wherein the numerical combining processing comprises:

selecting two of the columns in the second spectrum matrix;

using a plurality of values of leftmost one of two selected columns as real part values of a plurality of complex numbers, and using a plurality of values of rightmost one of the two selected columns as imaginary part values of the plurality of complex numbers, wherein the plurality of complex numbers correspond to the plurality of frequency components respectively;

for the two selected columns, generating a combined spectrum array according to the plurality of frequencies and the plurality of complex numbers; and for the two selected columns, using the combined spectrum array as leftmost one of the two columns in the second spectrum matrix, and deleting rightmost one of the two columns in the second spectrum matrix.

6. The data processing device of claim 1, wherein the processor further runs a bidirectional encoder representations from transformers model, wherein the bidirectional encoder representations from transformers model is configured for performing:

replacing one of the plurality of first spectrum arrays with a masked array to generate a masked spectrum matrix;

replacing the one of the first spectrum arrays with a random array to generate a random spectrum matrix; and inputting the masked spectrum matrix, the random spectrum matrix and the first spectrum matrix into an encoder module in the transformer model to pre-train the encoder module.

7. The data processing device of claim 6, wherein the bidirectional encoder representations from transformers model comprises the encoder module, a first fully connected feedforward neural network and a second fully connected feedforward neural network.

8. The data processing device of claim 1, wherein the arterial blood pressure data is configured for indicating blood pressure of the user.

9. The data processing device of claim 1, wherein the first spectrogram matrix and the second spectrogram matrix have same dimension.

10. A data processing method, comprising:

illuminating wrist skin of a user;

detecting light intensity reflected by the wrist skin of the user;

calculating photoplethysmographic data from the light intensity;

running a transformer model, and performing a short-term Fourier transform on photoplethysmographic data to generate a first spectrogram matrix, wherein a plurality of columns in the first spectrogram matrix respectively correspond to a plurality of time segments, and each of the plurality of columns in the first spectrogram matrix comprises a plurality of frequency components on a corresponding time segment;

performing numerical split processing on the first spectrogram matrix to generate a first spectrum matrix, wherein the first spectrum matrix comprises a plurality of first spectrum arrays arranged in sequence from left to right;

inputting the plurality of first spectrum arrays into the transformer model from left to right to generate a plurality of second spectrum arrays in sequence, and transforming the plurality of second spectrum arrays into a second spectrum matrix according to an order in which the plurality of second spectrum arrays are generated, wherein the second spectrum arrays are columns in the second spectrum matrix from left to right;

performing numerical combining processing on the second spectrum matrix to generate a second spectrogram matrix; and performing inverse short-term Fourier transform on the second spectrogram matrix to generate arterial blood pressure data.

11. The data processing method of claim 10, wherein the transformer model comprises an encoder module, a decoder module, a first fully connected feedforward neural network and a second fully connected feedforward neural network, wherein the encoder module is configured for inputting the plurality of first spectrum arrays, and connected to the decoder module, and the decoder module is connected to the first fully connected feedforward neural network, and the first fully connected feedforward neural network is connected to the second fully connected feedforward neural network, and the second fully connected feedforward neural network is configured for outputting the plurality of second spectrum arrays, wherein the encoder module comprises a plurality of first hidden representation layers, and the decoder module comprises a plurality of second hidden representation layers.

12. The data processing method of claim 11, wherein the plurality of first hidden representation layers comprise a first self-attention layer and a first feedforward layer, and the plurality of second hidden representation layers comprise a second self-attention layer, an encoder-to-decoder self-attention layer and a second feedforward layer.

13. The data processing method of claim 10, wherein each of the plurality of columns in the first spectrogram matrix comprises a plurality of complex numbers respectively corresponding to the plurality of frequency components, wherein the numerical split processing comprises:

selecting one of the plurality of columns in the first spectrogram matrix from left to right, splitting the plurality of complex numbers of the one of the plurality of columns into a plurality of real part values and a plurality of imaginary part values, generating a real number spectrum array and an imaginary number spectrum array according to the plurality of real part values and the plurality of imaginary part values, using the real number spectrum array as the one of the columns, and inserting the imaginary number spectrum array to right of the one of the plurality of columns.

14. The data processing method of claim 10, wherein numerical combining processing comprises:

selecting two of the columns in the second spectrum matrix;

using a plurality of values of leftmost one of two selected columns as real part values of a plurality of complex numbers, and using a plurality of values of rightmost one of the two selected columns as imaginary part values of the plurality of complex numbers, wherein the plurality of complex numbers correspond to the plurality of frequency components respectively;

for the two selected columns, generating a combined spectrum array according to the plurality of frequencies and the plurality of complex numbers; and for the two selected columns, using the combined spectrum array as leftmost one of the two columns in the second spectrum matrix, and deleting rightmost one of the two columns in the second spectrum matrix.

15. The data processing method of claim 10, further comprising running a bidirectional encoder representations from transformers model, wherein the bidirectional encoder representations from transformers model is configured for performing:

replacing one of the plurality of first spectrum arrays with a masked array to generate a masked spectrum matrix;

replacing the one of the first spectrum arrays with a random array to generate a random spectrum matrix; and inputting the masked spectrum matrix, the random spectrum matrix and the first spectrum matrix into an encoder module in the transformer model to pre-train the encoder module.

16. The data processing method of claim 15, wherein the bidirectional encoder representations from transformers model comprises the encoder module, a first fully connected feedforward neural network and a second fully connected feedforward neural network.

17. The data processing method of claim 10, wherein the arterial blood pressure data is configured for indicating blood pressure of the user.

18. The data processing method of claim 10, wherein the first spectrogram matrix and the second spectrogram matrix have same dimension.

\* \* \* \* \*